(12) United States Patent
Kim

(10) Patent No.: US 11,304,984 B2
(45) Date of Patent: Apr. 19, 2022

(54) **PHARMACEUTICAL COMPOSITION COMPRISING *CODIUM FRAGILE* EXTRACT AS EFFECTIVE INGREDIENT FOR PROTECTING OR TREATING ARTICULAR CARTILAGE**

(71) Applicant: INDUSTRY ACADEMIC COOPERATION FOUNDATION CHOSUN UNIVERSITY, Gwangju (KR)

(72) Inventor: Chun Sung Kim, Gwangju (KR)

(73) Assignee: INDUSTRY ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 127 days.

(21) Appl. No.: 16/485,892

(22) PCT Filed: Feb. 7, 2018

(86) PCT No.: PCT/KR2018/001645
§ 371 (c)(1),
(2) Date: Aug. 14, 2019

(87) PCT Pub. No.: WO2018/151456
PCT Pub. Date: Aug. 23, 2018

(65) Prior Publication Data
US 2020/0016222 A1    Jan. 16, 2020

(30) Foreign Application Priority Data
Feb. 14, 2017 (KR) .......................... 10-2017-0020001

(51) Int. Cl.
*A61K 36/05* (2006.01)
*A61P 19/02* (2006.01)

(52) U.S. Cl.
CPC .............. *A61K 36/05* (2013.01); *A61P 19/02* (2018.01)

(58) Field of Classification Search
None
See application file for complete search history.

(56) References Cited

U.S. PATENT DOCUMENTS

| | | | |
|---|---|---|---|
| 9,119,870 B2* | 9/2015 | Arad | A61P 19/06 |
| 10,821,144 B2* | 11/2020 | Demais | A61P 25/28 |
| 10,912,805 B2* | 2/2021 | Demais | A61P 37/04 |
| 2005/0196410 A1* | 9/2005 | Daniels | A61K 36/05 |
| | | | 424/195.17 |

FOREIGN PATENT DOCUMENTS

| | | |
|---|---|---|
| CN | 103622990 A | 3/2014 |
| KR | 10-2004-0057103 A | 7/2004 |
| KR | 10-2011-0108916 A | 10/2011 |
| KR | 10-2012-0077267 A | 7/2012 |
| KR | 10-2014-0067826 A | 6/2014 |
| KR | 10-1571792 B1 | 11/2015 |
| KR | 10-2015-0138565 A | 12/2015 |

OTHER PUBLICATIONS

Wang et al. (2013) Intern. J. Biol. Macromolecules 57: 26-29. (Year: 2013).*
Love et al. (1964) J. Chem. Soc., 3338-3345. (Year: 1964).*
Tabarsa et al. (2013) Intern. J. Biol. Macromolecules, 59: 1-12. (Year: 2013).*
Qi et al. (2017) Intern. J. Biol. Macromolecules 95: 106-114. (Year: 2017).*
International Search Report for PCT/KR2018/001645 dated May 23, 2018.
Park, Mi Hwa et al., "Effect of Codium Fragile Extract on Collagen Content and Collagen Cross-link Formation in Ovariectomized Rats.", Journal of Life Science, vol. 17. No. 7, pp. 931-936, 2007 (English translation of abstract is submitted herewith).
Seo, Seong Ho, "Isolation and Characterization of Rheumatoid Arthritis Inhibitor from *Codium fragile*", Korea University Master's thesis, pp. 1-66, 2004, See abstract; and figure 3. (English translation of abstract is submitted herewith).

* cited by examiner

*Primary Examiner* — Russell G Fiebig
(74) *Attorney, Agent, or Firm* — The PL Law Group, PLLC

(57) ABSTRACT

A pharmaceutical composition includes a hot-water extract of *Codium fragile* as an effective ingredient for treating or preventing arthritis, which is a highly effective natural product-derived composition available for cosmetics, beverages, functional foods, etc. which are expected for the alleviation of arthritis.

1 Claim, 14 Drawing Sheets

MTT assay (B)

(A)

(B)

(A)

PHARMACEUTICAL COMPOSITION COMPRISING *CODIUM FRAGILE* EXTRACT AS EFFECTIVE INGREDIENT FOR PROTECTING OR TREATING ARTICULAR CARTILAGE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/001645, filed Feb. 7, 2018, which claims priority to the benefit of Korean Patent Application No. 10-2017-0020001 filed in the Korean Intellectual Property Office on Feb. 14, 2017, the entire contents of which are incorporated herein by reference.

TECHNICAL FIELD

The present invention relates to a pharmaceutical composition for protecting or treating articular cartilage, including a hot-water extract of *Codium fragile* as an effective ingredient.

BACKGROUND ART

Green algae are well known to provide a wide range of natural products having pharmacological activity. Sulfated polysaccharides (SPs) derived from the green algae have shown to have great potential to be used for development of anti-inflammatory or analgesic medication. *Codium fragile* is available as a dietary green algae belonging to codiales, and widely distributed along the coast of East Asia, Oceania and Northern Europe.

In South Korea, *Codium fragile* is a familiar one among seaweeds used in cooking and has also been used in treatment of enterobiasis, edema and urinary disorders such as dysuria in oriental medicine. Pyruvil and sulfated galactan isolated from *Codium fragile* are known to reduce mRNA and protein expression levels of inducible nitric oxide (iNOS) during nitrogen synthesis, and has been reported to inhibit mRNA and protein expression of IL-1β, IL-6 and TNF-α, which are known as pro-inflammatory cytokines.

Recently, some studies have reported that *Codium fragile* extract is helpful for health, and has anti-cancer, angiogenesis suppression and antioxidant efficacies. Further, ethanol or methanol extract of *Codium fragile* has been disclosed to inhibit NF-κB activity in mouse macrophage RAW264.7 cells, thereby suppressing inflammation.

Arthritis is a disease caused by inflammation and pain in joints, and may include degenerative arthritis (that is, 'osteoarthritis'), rheumatoid arthritis, gout, dry arthritis, etc., and 95% of the arthritis patient is afflicted with the degenerative arthritis. The degenerative arthritis is a disease that appears localized degenerative changes due to cartilage worn down, and also referred to as osteoarthritis. The osteoarthritis is a representative degenerated disease in close association with aging, and about 10 to 15% of the population, in particular, 60 to 80% of the elderly population over age of 60 suffers from the osteoarthritis.

Causes of the osteoarthritis are closely associated with aging or excess body weight, and more developed in women with getting older. Initial symptoms are a result of rigidity in one or two joints accompanied by throbbing pain, and when it is prolonged, hyperostosis or deformation of bones around the joint may be caused. A mechanism inducing the osteoarthritis may include increased generation of pro-inflammatory cytokines, and increase in secretion of MMPs such as collagenase, stromelysin, etc. to cause damage to articular cartilage matrix.

Current treatment of osteoarthritis used in clinical applications may be performed by therapeutic drugs such as analgesics, steroids, non-steroidal anti-inflammatory agents, etc. or cartilage protectors such as hyaluronic acid, glucosamine, chondroitin, etc., otherwise, surgical procedures such as arthroscopic surgery, high tibial osteotomy, partial joint arthroplasty, total knee arthroplasty, etc. However, the therapeutic agent has only non-specific effects of alleviating the pain and inflammation itself, while the cartilage protective agent only serves to protect the joints by supplying nutrients or mitigating impact to the cartilage.

Further, when taking the steroidal agent for a long period of time, it may cause side effects such as osteoporosis, hypertension, diabetes, etc. due to loss of calcium, and thus the drug treatment is used only for purpose of reducing a pain in most cases. Further, permanent replacement arthroplasty is mainly used now, and other drugs or surgical procedures to afford fundamental treatment effects have yet to be developed.

Rheumatoid arthritis is an inflammatory disease characterized by polyarthritis, and is known to have autoimmune phenomena as a main mechanism. Looking at the symptoms, the inflammation occurs in synovial membrane tissues, and macrophagocytes, dendritic cells, T lymphocytes, B lymphocytes, etc. move to the synovial tissues, which in turn, increase a synovial fluid to cause swollen and painful joints.

When the inflammation is continued and inflammatory synovial tissues are under hyperplasia, bone and cartilage are destructed to develop structural deformation of the joint and cause movement disorder. The rheumatoid arthritis may also have increased generation of pro-inflammatory cytokines and an increase in secretion of MMPs, and is known to destruct collagen and proteoglycan that form the articular cartilage, resulting in damage to the articular cartilage.

Inflammation is a first biological complex response of the human immune system to external pathogen, damage and infection while exposing to biological, chemical and physical stimulations. In order to oppose bacterial and viral infection, the body needs inflammation. However, excessive or persistent inflammation is associated with chronic inflammatory diseases such as inflammatory arthritis, atherosclerosis and asthma. An inflammatory process is typically characterized by gathering leukocytes and macrophages.

Lipopolysaccharides (LPS) quickly activate the macrophages and stimulate generation of pro-inflammatory cytokines as well as NO and prostaglandin E2 (PGE2) as inflammatory mediators. In particular, COX-2 significant for induction of inflammation reacts to factors such as LPS and the pro-inflammatory cytokines in the macrophages and thus increases quickly. Nuclear factor-kappa B (NF-κB) known as a signal transduction mechanism relevant to the inflammation is a positive modulator that responds to secretion of various pro-inflammatory cytokines and regulates expression of COX-2, and is also a dimer transcription regulator that regulates genes relevant to stress responses including inflammation, oxidative stress and apoptosis.

In physiological conditions, NF-κB is a hetero-dimer consisting of Rel A (p65) and NF-κB1 (p50) and located on cytoplasm in an inactive form as being bound to the inhibitor κB (IκB). However, NF-κB is phosphorylated in the inflammatory process, and then activated due to degradation of IκB. Thereafter, the NF-κB hetero-dimer quickly moves into a nucleus and activates gene expression of iNOS, COX-2 and the inflammatory cytokines (IL-1β, IL-6 and TNF-α).

Further, MAPKs path known as another inflammation-related signal transduction mechanism is well known to control conversion of stimulation of different cells into specific cellular responses such as cell proliferation, differentiation and survival. Three types of major MAPKs have been identified in mammalian with names of extracellular signal-regulated kinases (ERK-1/2), c-Jun N-terminal kinase (JNK) and p38. MAPK signal cascade due to activation of ERK, JNK and p38 may regulate phosphorylation to activate transcription factors such as AP-1 (cFos/cJun), ETS, RUNX-2, HIF-2α and C/EBPβ, all of which controls expression of genes involved in catabolism and inflammatory response along with NF-κB. Some studies demonstrate that MAPKs have an important role in activation of NF-κB. Therefore, blocking these paths may efficiently reduce arthritis and osteoarthritis caused by chronic inflammation.

Development of arthritis therapeutics using natural materials mostly includes manufacturing products using natural extracts, and an exact action mechanism has not been identified. Most of the products are easily taken in a form of oral agent and may be available for a long term use, thereby being actively developed. The materials under development currently may include, for example, hyaluronic acid with similar ingredients to the synovial fluid in an injection formulation, health dietary supplements such as glucosamine and chondroitin, and herbal medicines which are developed using natural materials disclosed in the existing herbal books such as 'Donguibogam,' the Korean ancient medical dictionary.

SUMMARY

It is an object of the present invention to provide an articular cartilage protective composition derived from natural materials with excellent effects, by obtaining a hot-water extract effective to improve inflammation and protect the articular cartilage from *Codium fragile* which has been mostly used as a seasoning for cooking in East Asia.

A hot-water extract of *Codium fragile* may suppress generation of nitric oxide (NO; also known to nitrogen monooxide) and expression of inducible nitric oxide synthase (iNOS) in mouse macropharges, is characterized by inhibiting expression of cyclooxygenase-2 (COX-2) protein and thus suppressing generation of prostaglandin $E_2$ ($PGE_2$), and further by inhibiting expression of IL-1β, IL_6 and TNF-α, which are known as pro-inflammatory cytokines. Further, it is possible to suppress generation of nitric oxide (NO) and to inhibit protein expression of inducible NO synthase (iNOS) in the cartilage cells isolated from knees of Sprague-Dawley rat. Further, protein expression by MMP-2, -9, -13 and ADMTS5 known as articular cartilage matrix degrading enzymes may also be inhibited. Further, it was found that synthesis of proteoglycan for constructing articular cartilage in monosodium iodoacetate (MIA)-derived arthritis-induced animals is increased.

The *Codium fragile* hot-water extract of the present invention suppresses phosphorylation and degradation of IκB-α to inhibit movement of p65 into nucleus, such that NF-κB signaling pathway may be inhibited and phosphorylation of MAPKs may be suppressed. Therefore, it is possible to provide a pharmaceutical composition for protection of articular cartilage with anti-inflammatory and articular protection effects.

Using an anti-inflammatory and articular cartilage protective composition, which includes *Codium fragile* extract as an effective ingredient, according to the present invention, may provide a natural material-derived composition with excellent anti-inflammatory and articular cartilage protective effects, whereby this composition may be used in functional foods, quasi-drug goods, beverages, etc. with expected inflammation improvement and articular cartilage protection effects.

DETAILED DESCRIPTION

Figure 1:
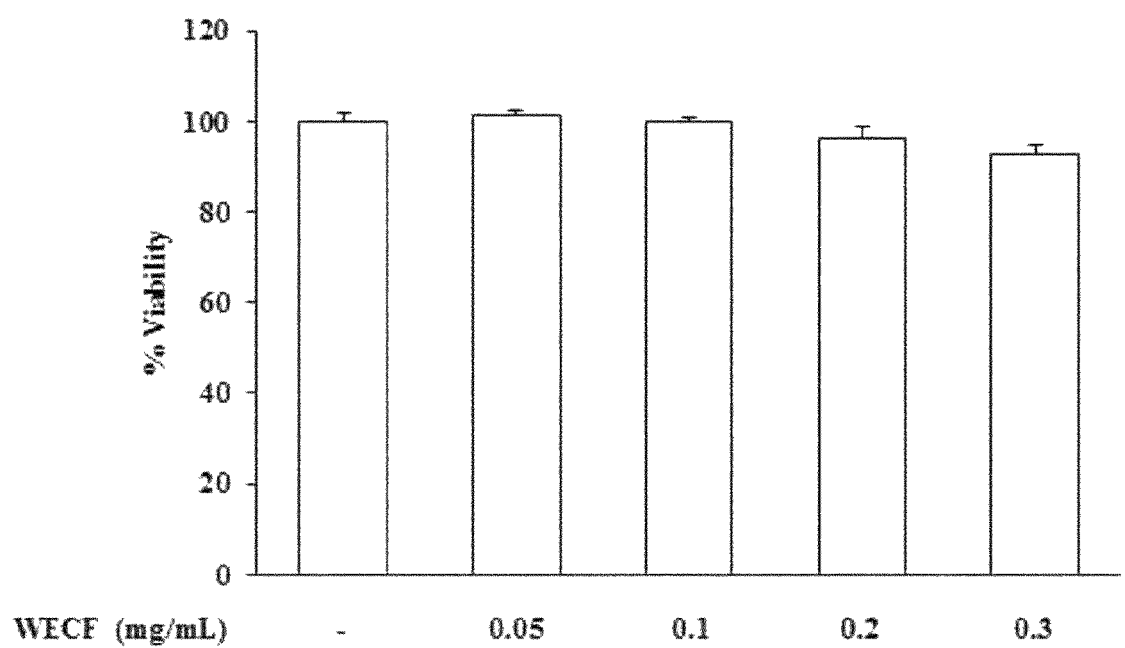
FIG. 1 is a graph illustrating effects of a hot-water extract of *Codium fragile* on viability of mouse macrophage RAW264.7 cells.

The present inventors have found that: a hot-water extract of *Codium fragile* exhibits inflammation inhibitory effects in RAW264.7 cell line stimulated with LPS; protein expression of aggrecan for constructing cartilage in chondrocytes isolated from knees of Sprague-Dawley rat is increased; further, protein expression of MMP-2, -9, -13 and ADMATS5 known as cartilage matrix degrading enzymes is inhibited.

Further, in an animal model with induction of a monosodium iodoacetate (MIA)-derived arthritis, it was found that expression of proteoglycan for constructing the joint is increased. In LPS-stimulated mouse macrophage RAW264.7 cell line, the activity of NF-κB and phosphorylation of MAPKs are inhibited thus to suppress generation of pro-inflammatory cytokines and mediators and to inhibit expression of articular cartilage matrix degrading enzymes, whereby an articular cartilage protective composition based on the hot-water extract of Codium fragile has been completed. Hereinafter, the present invention will be described in detail by way of particular embodiments.

I. Materials and Methods

1. Preparation of Water-Soluble Sulfated Polysaccharides Extract of C. fragile (WECF)

After washing fresh Codium fragile (C. fragile) collected from Wando beach on June 2016 in tap water three times to remove salt, sand and epiphytic plants attached to the surface, the washed C. fragile was dried using an air drier at 50° C. for 48 hours. The dried sample was then ground in a mill and a 20-fold volume of distilled water was added thereto, followed by extraction at 95° C. for 1 hour. Then, the extract was filtered through a 3M paper and lyophilized. The dried extract powders were dissolved in distilled water with 100 mg/ml, filtered through 0.2-μm syringe filter and then used in the present experiment.

2. Reagents Used in the Invention

LPS, 3-(4,5-dimethylthiazol-2-yl)-2,5-diphenyltetrazolium (MTT), sulfanilamide, N-(1-naphthyl) ethylendiamine dihydrochloride and phosphoric acid were purchased from Sigma-Aldrich Co. (St. Louis, Mo.), Dulbecco's Modified Eagle's medium (DMEM), Dulbecco's Modified Eagle's medium (DMEM)/F12 and penicillin-streptomycin solution were purchased from WelGene (Deagu, Republic of Korea). Further, fetal bovine serum (FBS) was purchased from Corning (Corning, N.Y.), an antibody to anti-iNOS was purchased from Abcam (Cambridge, Mass.), and primary and secondary antibodies except for anti-iNOS were purchased from Technology (Danvers, Mass., USA), respectively.

3. Cell Culture and Cell Viability Measurement

RAW264.7 cell line of a mouse macrophage cell line was distributed from Korea Research Institute of Bioscience and Biotechnology (KRIBB, Daejeon, Republic of Korea) and cultured in a 5% carbon dioxide incubator at 37° C. wherein Dulbecco's Modified Eagle's medium (DMEM)/F12 medium containing 10% FBS and 1% penicillin/streptomycin is included and humidity is controlled. Alternatively, chondrocytes obtained from knees of Sprague-Dawley rat at 3 days of age were cultured in a 5% carbon dioxide incubator at 37° C. wherein Dulbecco's Modified Eagle's medium (DMEM)/F12 medium containing 10% FBS and 1% penicillin/streptomycin is included and humidity is controlled. For assessment of cell viability, the cells were cultured in 6 well plate with $1 \times 10^5$ cells/ml for 6 hours, and then, treated with WECF prepared above at various concentrations for 24 hours. After treatment using the C. fragile, the cell viability was determined by MTT assay.

4. Measurement of Nitric Oxide (NO)

RAW264.7 cell lines of a mouse macrophage RAW264.7 cell line and primary-cultured chondrocytes of Sprague-Dawley rat were cultured in 6 well plate with $1 \times 10^5$ cells/ml, respectively. The cultured cells, respectively, were treated with WECF at various concentrations for 1 hour, followed by treatment with LPS (0.2 μg/ml) and IL-1β (20 ng/ml), respectively, and culturing the same for 24 hours. Nitrite accumulated in the culture medium was measured as an index of NO generation on the basis of Griess reaction. Briefly, 100 μL of a supernatant in the plate after treatment with WECF at various concentrations was mixed with equal volume of Griess reagent (1% [w/v] sulfanilamide in 5% [v/v] phosphoric acid and 0.1% [w/v] naphthylethylenediamine) in a dark room for 10 minutes. Then, an absorbance at 540 nm was measured by a microplate reader (Epoch Bioteck; Bio-Tek Instruments Inc., Winooski, Vt.). A concentration of nitrite was determined by comparison with a standard curve for sodium nitrite.

5. Isolation of Total RNA and Reverse Transcriptase Polymerase Chain Reaction (Reverse-Transcriptase PCR)

Using trizol reagent (Invitrogen, Carlsbad, Calif.), total RNA was isolated from each cell. Using Prime Script™ 1 st strand cDNA synthesis kit (Takara Bio Inc., Otsu, Japan), cDNA was synthesized from 1 μg of the total RNA followed by identification of RNA expression using a variety of primers.

6. Separation of Nuclear Protein and Cytoplasmic Protein

After treating RAW264.7 cells with WECF for 1 hour, the cells were further treated with LPS (0.2 μg/ml) and IL-1β (20 ng/ml) and then incubated for 24 hours. After recovery, the cells were washed with cold PBS 2 times. The cells were dissolved using NEPER ™ nucleus an d cytoplasm extraction reagent kit (Thermo Scientific, Ill., USA) in accordance with the product manual. Briefly, the cells were re-suspend in the reagent, centrifuged at 4° C. and 15,000 g for 5 minutes, and the supernatant containing the cytoplasmic fraction was transferred to a clean tube. Then, after removing contaminants from the pellets containing nuclei, the pellets were re-suspended in NER reagent, followed by centrifugation at 4° C. and 15,000 g for 10 minutes. The supernatant thereof was used as a nuclear fraction. A protein concentration of each extract was quantified by BCA protein measurement kit (Pierce, Thermo Scientific, Ill., USA).

7. Identification of Protein Expression

The cells obtained above were dissolved in a protein extraction reagent on ice fir 30 minutes. After centrifugation at 4° C. and 12,000 g for 15 minutes (Sorvall centrifuge, Bad Homburg, Germany), the supernatant thereof was transferred to a new tube. A protein concentration was quantified by BCA protein assay kit (Pierce, Thermo Scientific, Ill., USA) on BSA standard curve.

About 30 μg of protein from each cell lysate was dissolved in Laemmli sample buffer, and then, loaded into 3 to 8% or 4 to 20% SDS-PAGE gel (Invitrogen Life Technologies). After electrophoresis of the protein at 120 V for 90 minutes, the separated protein was transferred to a nanofiber membrane including polyvinylidene difluoride (Amomedi, Gwangju, Korea).

After blocking the membrane with 5% BSA at room temperature for 1 hour, the membrane was reacted with a primary antibody to anti-IL-1β, anti-IL-6, anti-TNF-α, anti-iNOS, anti-COX-2, anti-total MAPKs (Cell Signaling Technology, Danvers, Mass., USA) and anti-β-actin (sc-47778, Santa Cruz Biotechnology, Santa Cruz, Calif., USA) for 15 hours. Then, after washing with TBS-T (0.1% Tween-20, 50 μM Tris-HCl pH 7.5, 150 μM NaCl) three times, the membrane was incubated with a secondary antibody for 1 hour, followed by washing again with TBS-T three times. Next, a protein was detected using WestSave Up ECL kit (AB Frontier, Seoul, Korea) and visualized using Microchemi 4.2 device (DNR Bioimaging Systems, Jerusalem, Israel).

8. Statistical Analysis

Results obtained from the above procedure are exhibited by a mean±standard deviation. After one-way variance analysis (One-way ANOVA), multiple comparison was implemented by Dunnett's t-test using GraphPad Prism (GraphPad Software Inc., Calif., USA). Statistical significance is marked by * when $p<0.05$,  when $p<0.01$, and * when $p<0.001$.

II. Experiment Result

FIG. 1 is a graph illustrating effects of a hot-water extract of *Codium fragile* on viability of mouse macrophage RAW264.7 cells. In this regard, RAW264.7 cells were treated with WECF at various concentrations (0.05, 0.1, 0.2, 0.3, and 0.5 mg/ml) for 24 hours. Cell viability was determined by MTT assay. Results thereof are given as a percentage to the control group. Each result is exhibited by a mean±standard deviation (SD) of three repeated experiments (**$p<0.01$).

Figure 2:
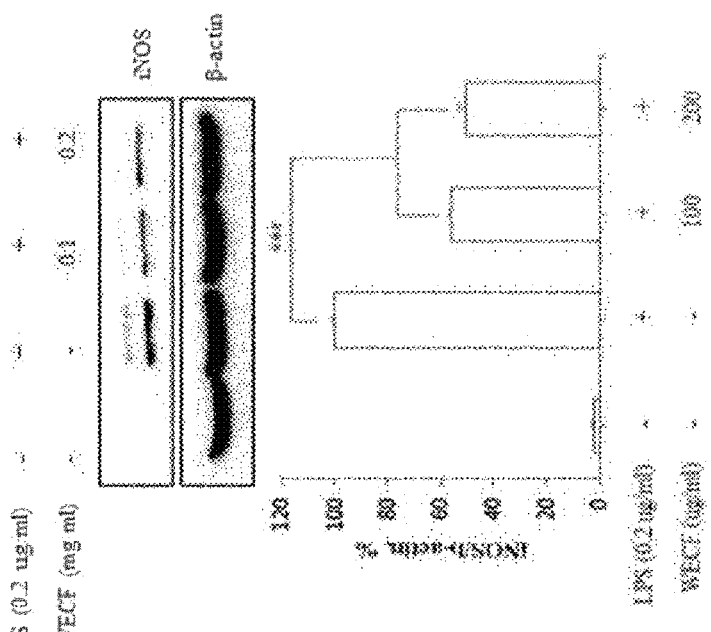
FIG. 2 illustrates inhibitory effects of the hot-water extract of *Codium fragile* on levels of nitric oxide (hereinafter referred to as NO) and inducible NO synthase (iNOS) induced by LPS in the mouse macrophage RAW264.7 cells.
Figure 2:
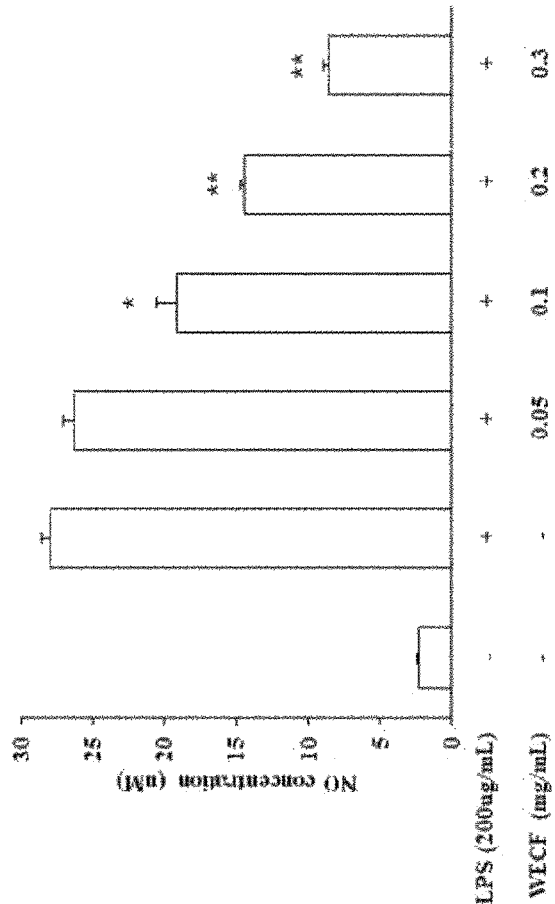

FIG. 2 illustrates inhibitory effects of the hot-water extract of *Codium fragile* on levels of NO and inducible NO synthase (iNOS) induced by LPS in the mouse macrophage RAW264.7 cells. In this regard, (A) of FIG. 2 shows that WECF inhibited NO level stimulated with LPS in the RAW264.7 cells. After pre-treatment of RAW264.7 cells with WECF (0.05, 0.1, 0.2, 0.3, and 0.5 mg/ml) for 1 hour, the cells were stimulated with LPS (0.2 mg/ml) for 24 hours. An amount of NO generation in the cell culture medium was measured using Griess reagent. (B) of FIG. 2 shows that WECF inhibited protein expression level of iNOS in the RAW264.7 cells stimulated with LPS. The protein expression of iNOS was confirmed by western blot analysis wherein β-actin was used as a control group. Quantification of protein expression was implemented using J-software. Results thereof are exhibited by a mean±SD of three repeated experiments. Statistical analysis was determined by Dunnett's t-test ( * Compared with the LPS, $p<0.01$, and *$p<0.001$).

Figure 3:
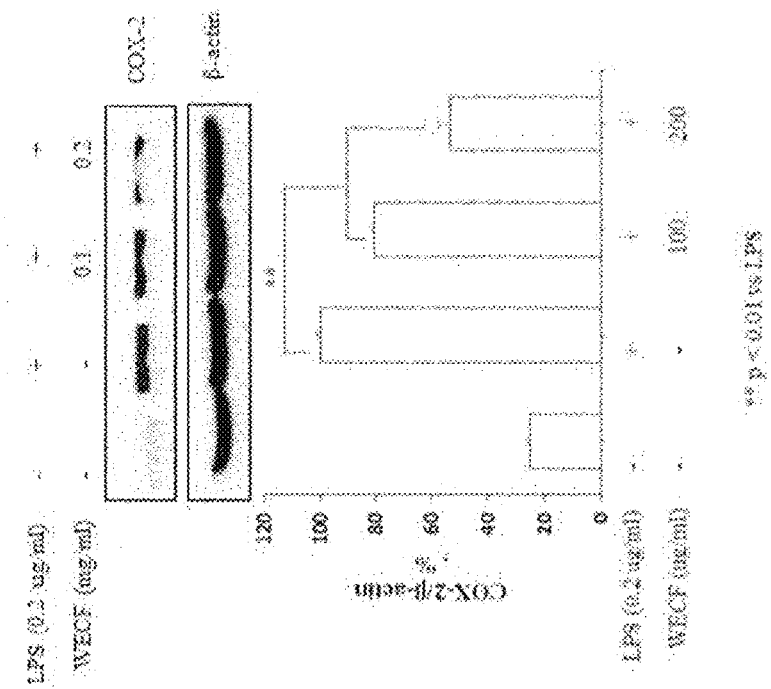
FIG. 3 illustrates inhibitory effects of the hot-water extract of *Codium fragile* to prostaglandin $E_2$ ($PGE_2$) and cyclooxygenase-2 induced by LPS in the mouse macrophage RAW264.7 cells.
Figure 3:
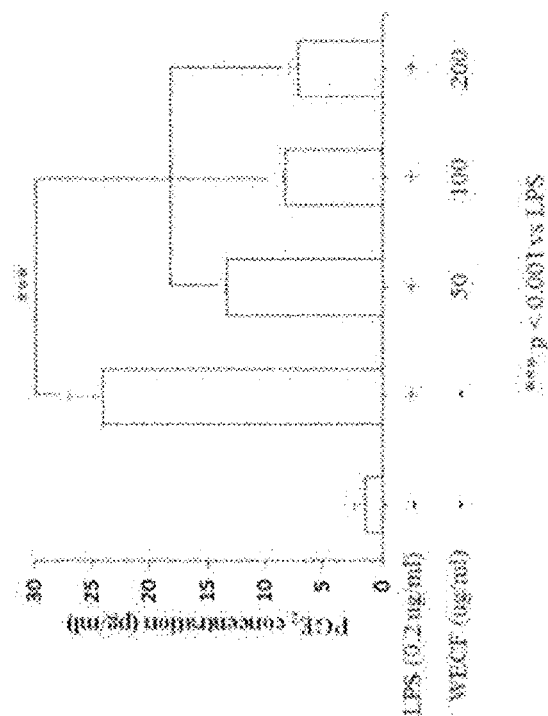

FIG. 3 illustrates inhibitory effects of the hot-water extract of *Codium fragile* to prostaglandin $E_2$ ($PGE_2$) and cyclooxygenase-2 induced by LPS in the mouse macrophage RAW264.7 cells. In this regard, (A) of FIG. 3 shows that WECF inhibited prostaglandin $E_2$ ($PGE_2$) induced by LPS in RAW264.7 cell line. The cells were pre-treated with WECF (0.5, 0.1, and 0.2 mg/ml) for 1 hour, and then, stimulated with LPS (0.2 mg/ml) for 24 hours. PGE2 generation in the cell culture medium was confirmed by ELISA assay. (B) of FIG. 3 shows that WECF inhibited protein expression level of cyclooxygenase (COX)-2 induced by LPS in RAW264.7 cell line. RAW264.7 cells were pre-treated with WECF (0.1, and 0.2 mg/ml) for 1 hour, and then, stimulated with LPS (0.2 mg/ml) for 24 hours. Protein expression of COX-2 was confirmed by western blot analysis wherein β-actin was used as a control group. Quantification of protein expression was implemented using J-software. Results thereof are exhibited by a mean±SD of three repeated experiments. Statistical analysis was determined by Dunnett's t-test ( * Compared with the LPS, $p<0.01$, and *$p<0.001$).

Figure 4:
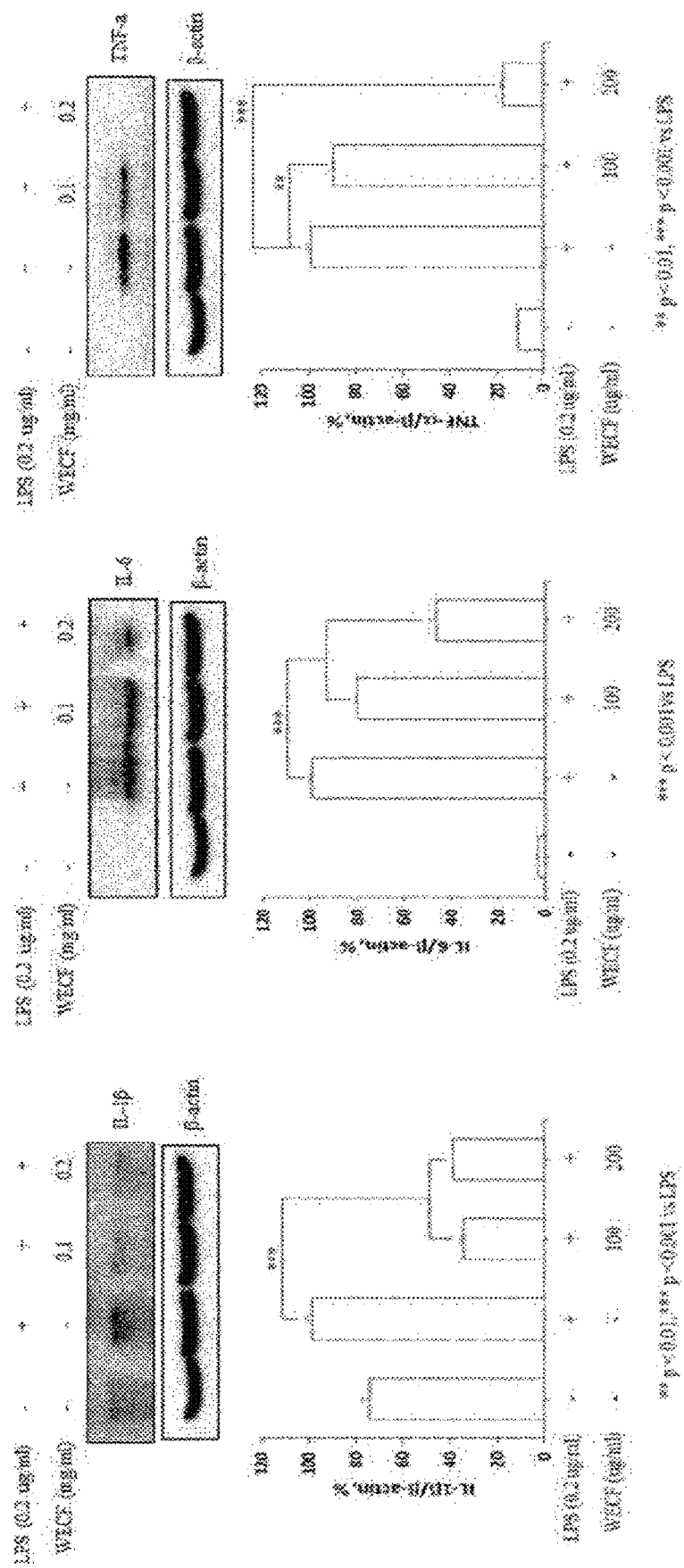
FIG. 4 illustrates inhibitory effects of the hot-water extract of *Codium fragile* to pro-inflammatory cytokine induced by LPS in the mouse macrophage RAW264.7 cells.

FIG. 4 illustrates inhibitory effects of the hot-water extract of *Codium fragile* to pro-inflammatory cytokines induced by LPS in the mouse macrophage RAW264.7 cells. In this regard, WECF inhibited protein levels of TNF-α, IL-1β and IL-6 induced by LPS in RAW264.7 cells. The cells were pre-treated with WECF (0.1, and 0.2 mg/ml) for 1 hour, and then, stimulated with LPS (0.2 mg/ml) for 24 hours. The control group used herein was β-actin. Results of A (B, C, D, F, G, H) and E were subjected to quantitative analysis using Image J-software, and exhibited by a mean±SD of three repeated experiments. Symbol * represents statistically significant difference as compared to LPS-treated group (***$p<0.001$).

Figure 5:
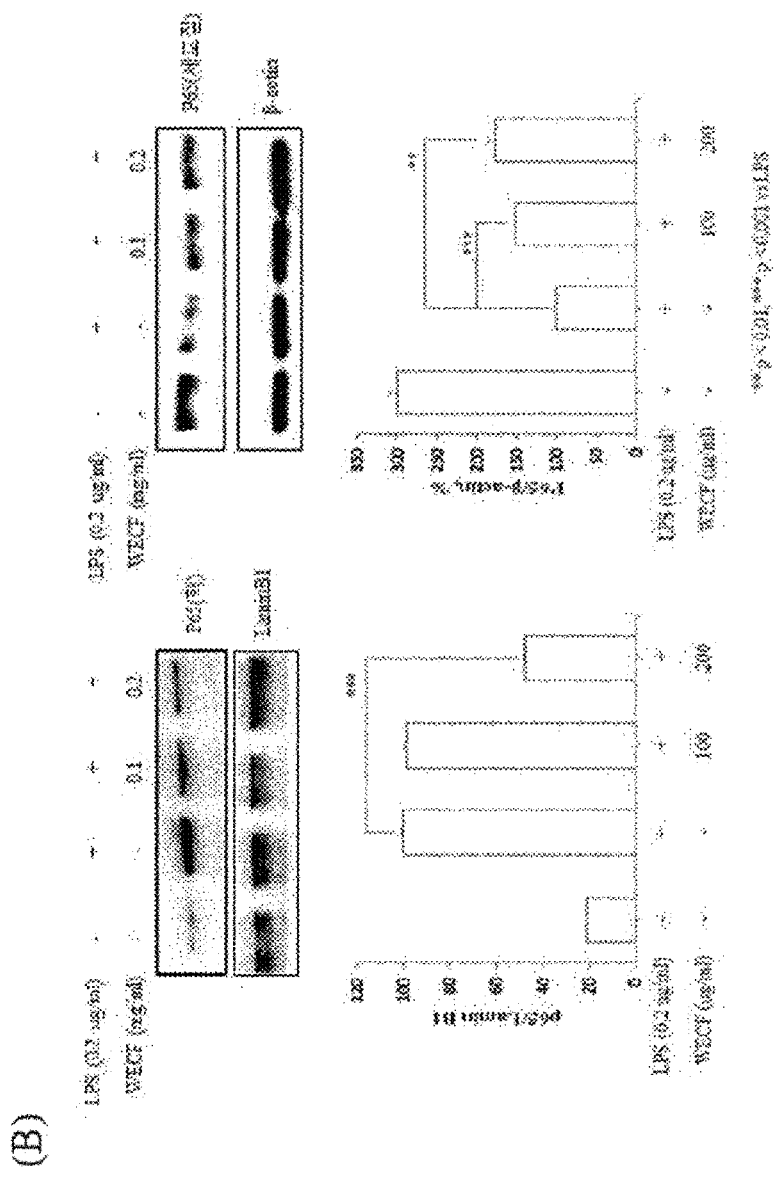
FIG. 5 illustrates effects of the hot-water extract of *Codium fragile* on phosphorylation of IκB-αinduced by LPS and movement activity of NF-κB into nucleus in RAW264.7 cells.

FIG. 5 illustrates effects of the hot-water extract of *Codium fragile* on phosphorylation of IκB-α induced by LPS and movement activity of NF-κB into nucleus in RAW264.7 cells. In this regard, (A) of FIG. 5 shows that WECF inhibited phosphorylation of IκB-α induced by LPS. Protein Expression of IκB-α and p-IκB-α was confirmed by western blot analysis. Results of A were quantitatively analyzed using Image J-software. (B) of FIG. 5 shows that WECF inhibited movement of NF-κB induced by LPS into nuclei. The cells were pre-treated with WECF (0.1, and 0.2 mg/ml) for 1 hour, and then, stimulated with LPS (0.2 mg/ml) for 24 hours. Protein expression level of NF-κB (p65) separated from the nucleus and the cytoplasm was confirmed by western blot analysis. β-actin and Lamin B1 were used as a control group in relation to the cytoplasmic and nuclear proteins. All of results were quantitatively analyzed using Image J-software. Results thereof are exhibited by a mean±SD of three repeated experiments. Symbol * represents statistically significant difference as compared to LPS treatment groups ($p<0.01$, and *$p<0.001$).

Figure 6:
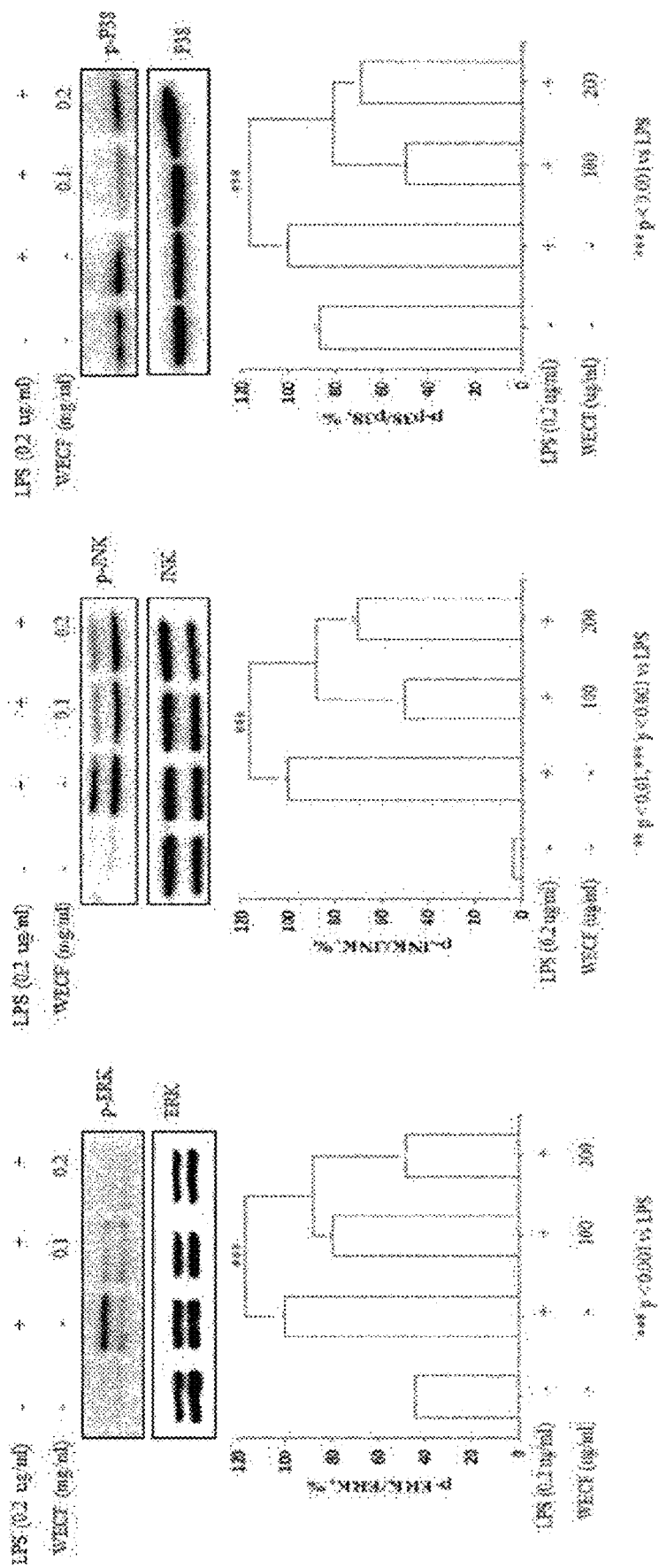
FIG. 6 illustrates effects of the hot-water extract of *Codium fragile* on phosphorylation of MAPKs (ERK, JNK, and p38) induced by LPS in the mouse macrophage RAW264.7 cells.

FIG. 6 illustrates effects of the hot-water extract of *Codium fragile* on phosphorylation of MAPKs (ERK, JNK, and p38) induced by LPS in the mouse macrophage RAW264.7 cells. WECF inhibited phosphorylation of ERK, JNK and p38 induced by LPS. The cells were pre-treated with WECF (0.1, and 0.2 mg/ml) for 1 hour, and then, stimulated with LPS (0.2 mg/ml) for 24 hours. ERK, JNK and p38 were confirmed by western blot analysis using specific antibodies. Results of A were quantitatively analyzed using Image J-software. Results thereof are exhibited by a mean±SD of three repeated experiments. Symbol * represents statistically significant difference as compared to the LPS-treated group ($p<0.01$, and *$p<0.001$).

Figure 7:
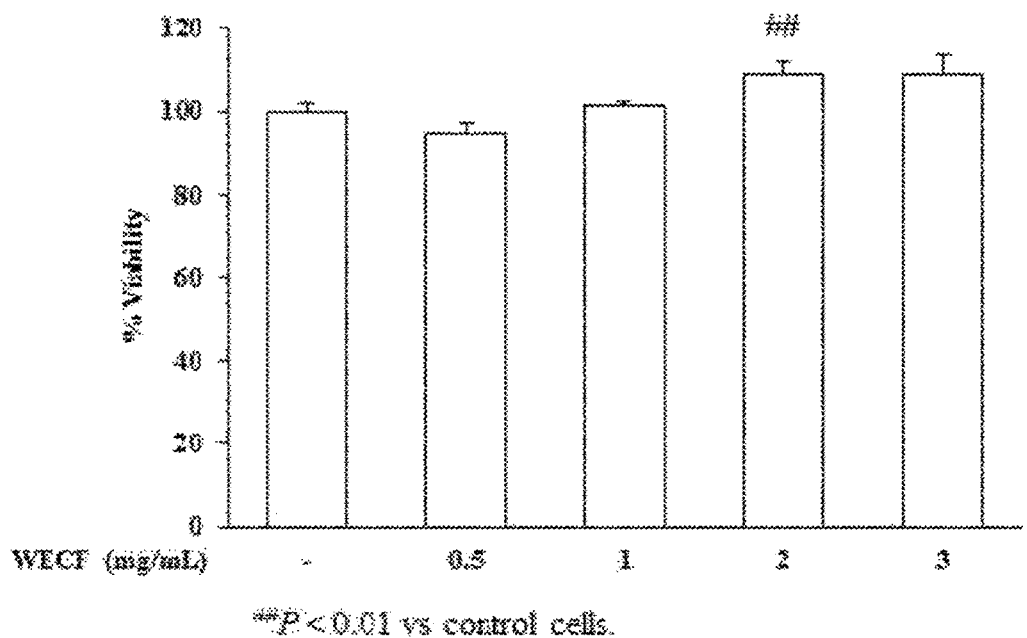
FIG. 7 is a graph illustrating effects of the hot-water extract of *Codium fragile* on viability of primary-cultured chondrocytes of Sprague-Dawley rat.

FIG. 7 is a graph illustrating effects of the hot-water extract of *Codium fragile* on viability of primary-cultured chondrocytes of Sprague-Dawley rat. The primary-cultured chondrocytes were treated with WECF at various concentrations (0.5, 1, 2, and 3 mg/ml) for 24 hours. Cell viability was determined by MTT assay. Results thereof are given as a percentage to the control group. Each result is exhibited by a mean±SD of three repeated experiments (**$p<0.01$).

Figure 8:
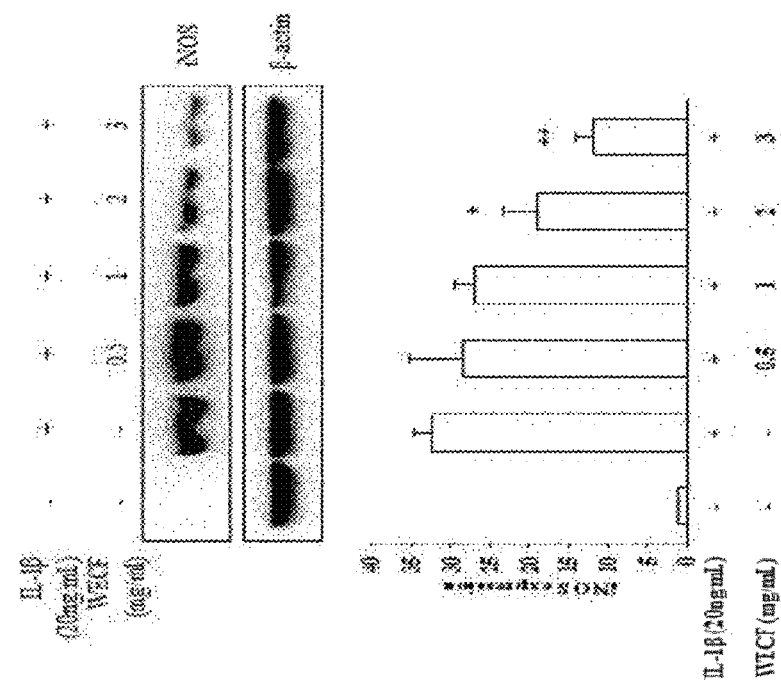
FIG. 8 illustrates inhibitory effects of the hot-water extract of *Codium fragile* on levels of NO and inducible NO (iNOS) induced by IL-1β (20 ng/ml) in primary-cultured chondrocytes of Sprague-Dawley rat.
Figure 8:
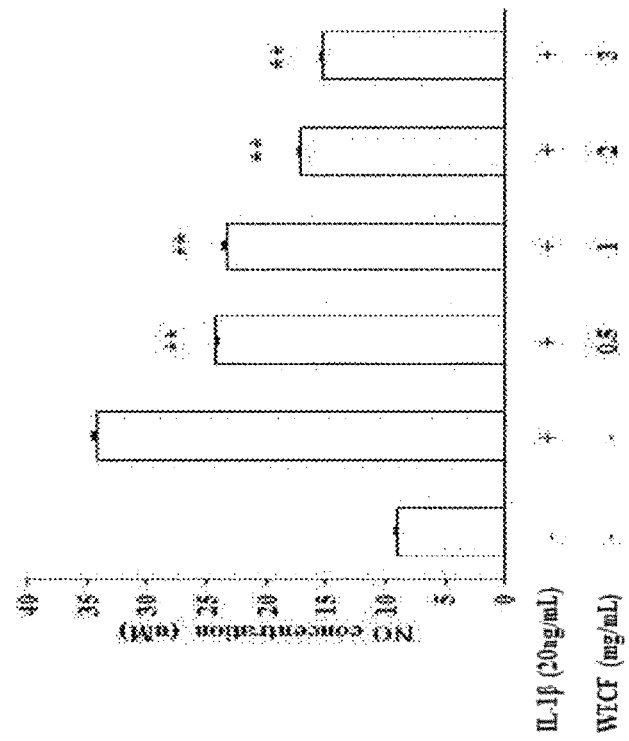

FIG. 8 illustrates inhibitory effects of the hot-water extract of *Codium fragile* on levels of NO and inducible NO (iNOS) induced by IL-1β (20 ng/ml) in primary-cultured chondrocytes of Sprague-Dawley rat. In this regard, (A) of FIG. 8 shows that WECF inhibited NO level stimulated by IL-1β (20 ng/ml) in the chondrocytes. The chondrocytes were pre-treated with WECF (0.5, 1, 2, and 3 mg/ml) for 1 hour, and then, stimulated with IL-1β (20 ng/ml) for 24 hours. An amount of NO generation in the cell culture medium was measured using Griess reagent. (B) of FIG. 8 shows that WECF inhibited protein expression level of iNOS in the chondrocytes stimulated with IL-1β (20 ng/ml). The protein expression of iNOS was confirmed by western blot analysis wherein β-actin was used as a control group. Quantification of protein expression was implemented using J-software. Results thereof are exhibited by a mean±SD of three repeated experiments. Statistical analysis was determined by Dunnett's t-test ( * Compared with the LPS, $p<0.01$, and *$p<0.001$).

Figure 9:
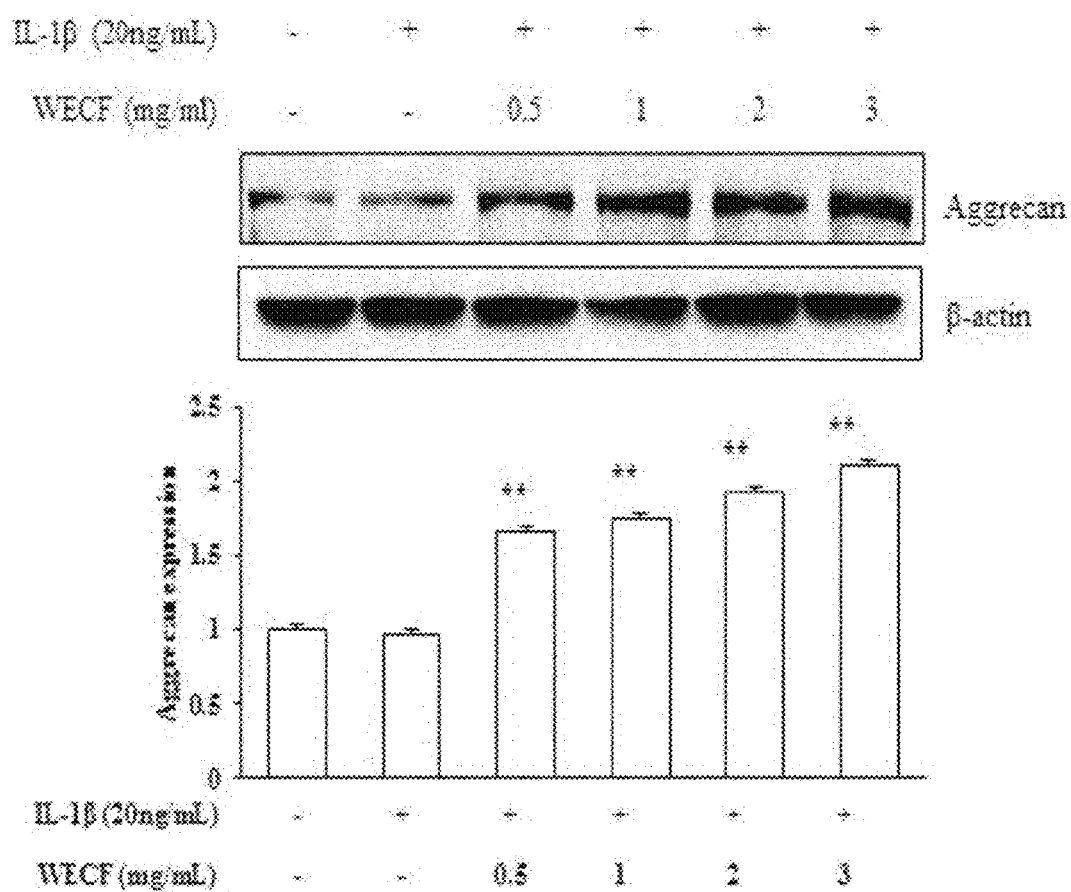
FIG. 9 illustrates effects of the hot-water extract of *Codium fragile* to increase protein expression of aggrecan, which is known as a cartilage constituent, induced by IL-1β (20 ng/ml) in the primary-cultured chondrocytes of Sprague-Dawley rat.

FIG. 9 illustrates effects of the hot-water extract of *Codium fragile* to increase protein expression of aggrecan, which is known as a cartilage constituent, induced by IL-1β (20 ng/ml) in the primary-cultured chondrocytes of Sprague-Dawley rat. The chondrocytes was pre-treated with WECF (0.5, 1, 2, and 3 mg/ml) for 1 hour, and then, stimulated with IL-1β (20 ng/ml) for 24 hours. Using IL-1β (20 ng/ml) only, which is known as an inflammation induction factor, for treatment, the protein expression of aggrecan was slightly reduced, however, the treated group with WECF (0.5, 1, 2, and 3 mg/ml) showed increased protein expression of aggrecan. The control group used herein was β-actin. Quantitative analysis was implemented using Image J-software, and results thereof are exhibited by a mean±SD of three repeated experiments. Symbol * represents statistically significant difference as compared to IL-1β (20 ng/ml) treated group (***p<0.001).

Figure 10:
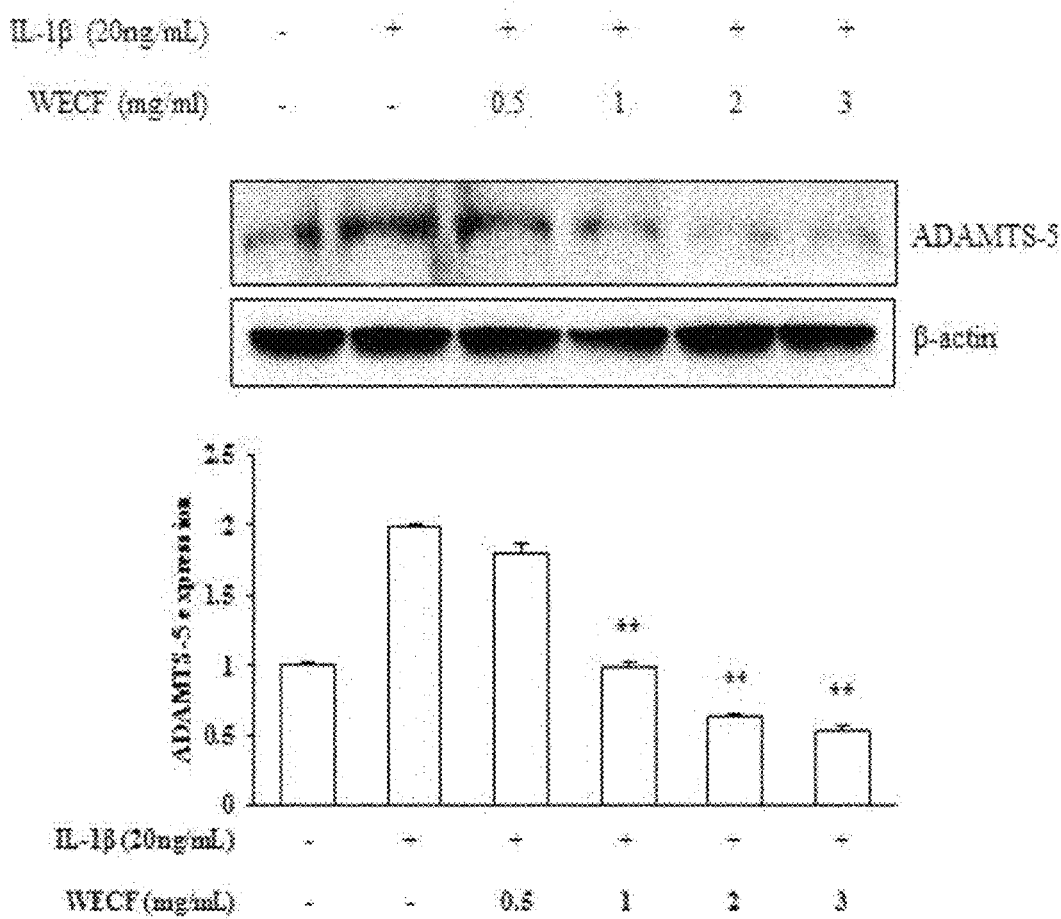
FIG. 10 illustrates inhibitory effects of the hot-water extract of *Codium fragile* on protein expression of ADMTS5, which is known as an enzyme for degrading articular cartilage matrix, induced by IL-1β (20 ng/ml) in the primary-cultured chondrocytes of Sprague-Dawley rat.

FIG. 10 illustrates inhibitory effects of the hot-water extract of *Codium fragile* on protein expression of ADMTS5, which is known as an enzyme for degrading articular cartilage matrix, induced by IL-1β (20 ng/ml) in the primary-cultured chondrocytes of Sprague-Dawley rat. The chondrocytes were pre-treated with WECF (0.5, 1, 2, and 3 mg/ml) for 1 hour, and then, stimulated with IL-1β (20 ng/ml) for 24 hours. Using IL-1β (20 ng/ml) only, which is known as an inflammation induction factor, for treatment, the protein expression of ADAMTS5 was significantly increased, however, the chondrocytes treated with WECF (0.5, 1, 2, and 3 mg/ml) showed a reduction in protein expression of ADAMTS5 depending upon concentrations. The control group used herein was β-actin. Quantitative analysis was implemented using Image J-software, and results thereof are exhibited by a mean±SD of three repeated experiments. Symbol * represents statistically significant difference as compared to IL-1β (20 ng/ml) treated group (***p<0.001).

Figure 11:
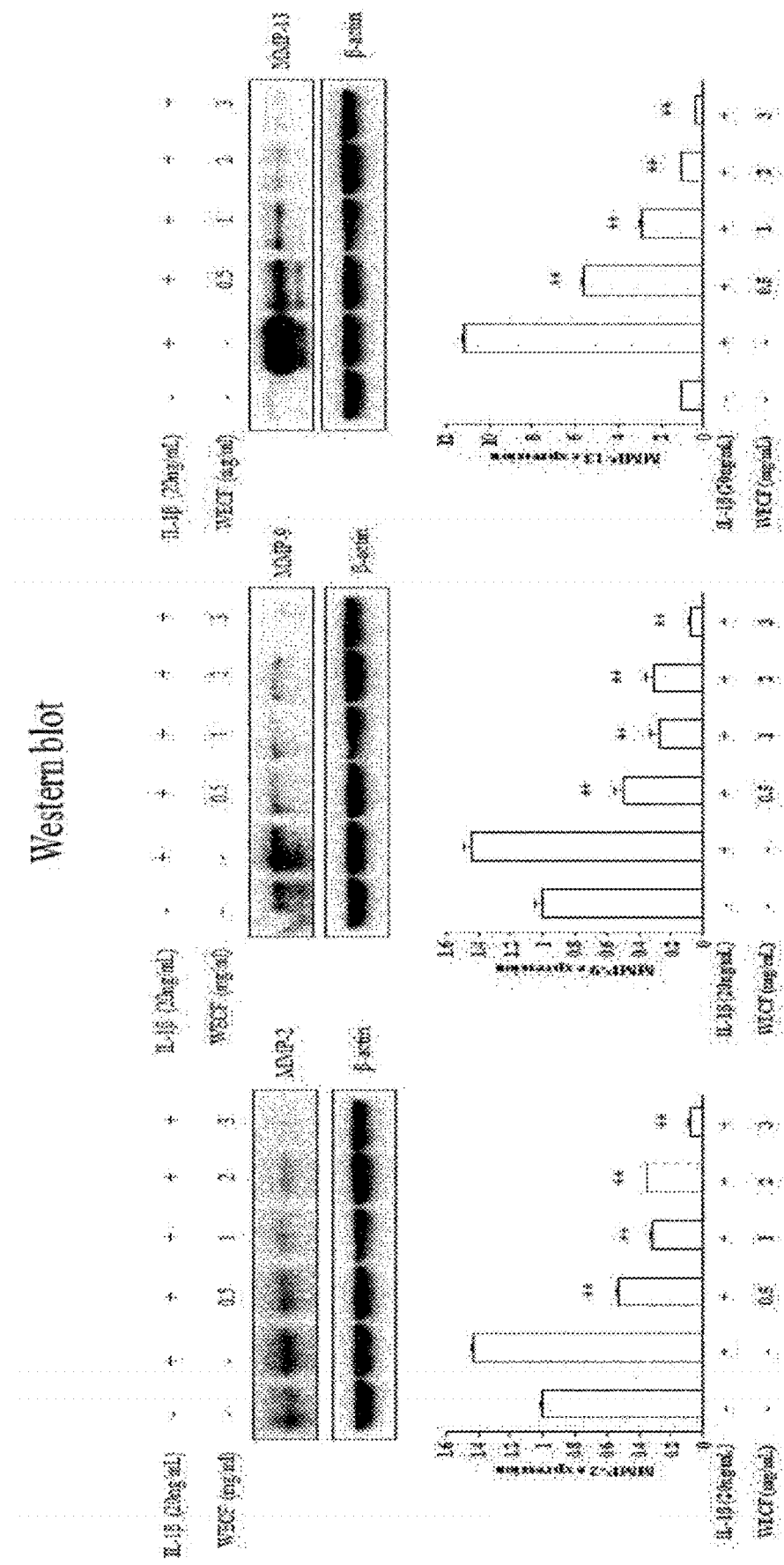
FIG. 11 illustrates inhibitory effects of the hot-water extract of *Codium fragile* on protein expression of MMP-2, -9 and -13, which are known as enzymes for degrading articular cartilage matrix, induced by IL-1β (20 ng/ml) in the primary-cultured chondrocytes of Sprague-Dawley rat.

FIG. 11 illustrates inhibitory effects of the hot-water extract of *Codium fragile* on protein expression of MMP-2, -9 and -13, which are known as enzymes for degrading articular cartilage matrix, induced by IL-1β (20 ng/ml) in the primary-cultured chondrocytes of Sprague-Dawley rat. The chondrocytes were pre-treated with WECF (0.5, 1, 2, and 3 mg/ml) for 1 hour, and then, stimulated with IL-1β (20 ng/ml) for 24 hours. Using IL-1β (20 ng/ml) only, which is known as an inflammation induction factor, for treatment, the protein expression of MMP-2, -9 and -13 was significantly increased, however, the chondrocytes treated with WECF (0.5, 1, 2, and 3 mg/ml) showed a reduction in protein expression of MMP-2, -9 and -13 depending upon concentrations. The control group herein was β-actin. Quantitative analysis was implemented using Image J-software, and results thereof are exhibited by a mean±SD of three repeated experiments. Symbol * represents statistically significant difference as compared to IL-1β (20 ng/ml) treated group (***p<0.001).

Figure 12:
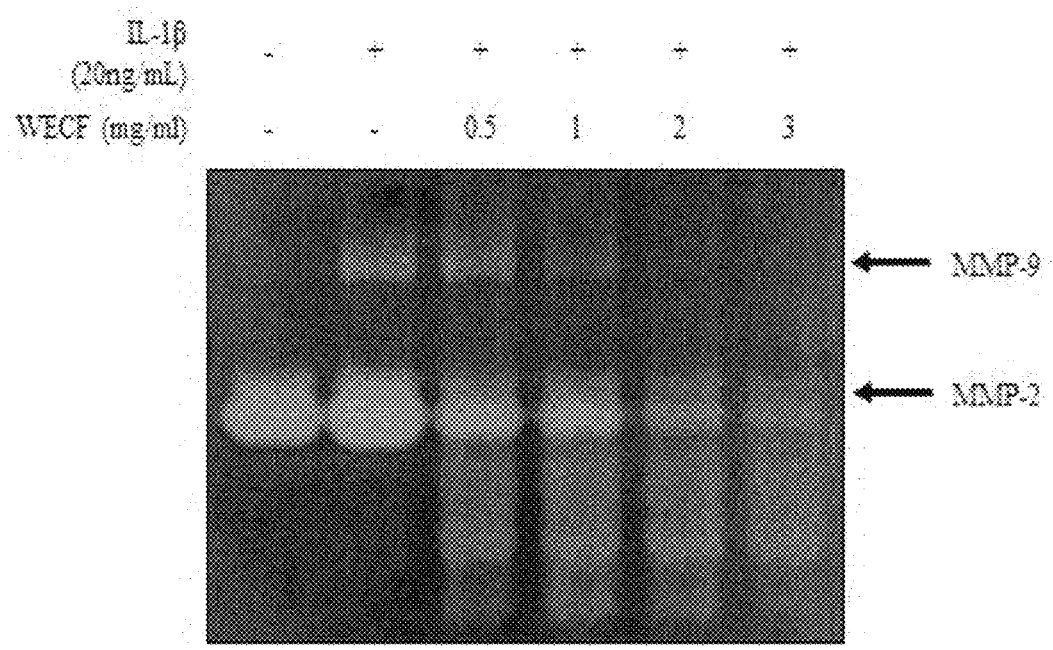
FIG. 12 illustrates effects of the hot-water extract of *Codium fragile* to suppress MMP-2, and -9 protein degrading enzymes ('proteolytic enzymes'), induced by IL-1β (20 ng/ml) in the primary-cultured chondrocytes of Sprague-Dawley rat, followed by gelatin zymography.

FIG. 12 illustrates inhibitory effects of the hot-water extract of *Codium fragile* to MMP-2 and -9 proteolytic enzymes, induced by IL-1β (20 ng/ml) in the primary-cultured chondrocytes of Sprague-Dawley rat, followed by gelatin zymography. The chondrocytes were pre-treated with WECF (0.5, 1, 2, and 3 mg/ml) for 1 hour, and then, stimulated with IL-1β (20 ng/ml) for 24 hours. Using IL-1β (20 ng/ml) only, which is known as an inflammation induction factor, for treatment, MMP-2 and -9 proteolytic enzymes were significantly increased, however, the chondrocytes treated with WECF (0.5, 1, 2, and 3 mg/ml) showed a reduction in MMP-2 and -9 proteolytic enzymes depending upon concentrations.

Figure 13:
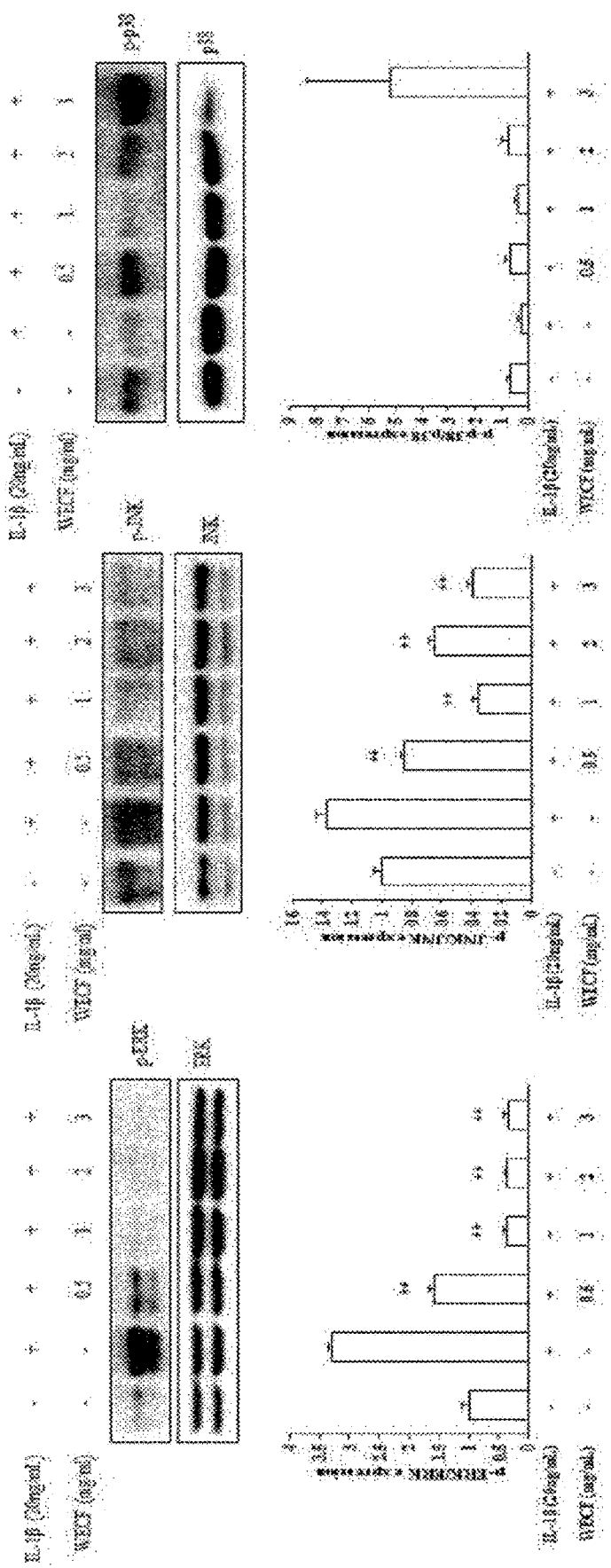
FIG. 13 illustrates inhibitory effects of the hot-water extract of *Codium fragile* on phophoryltion of MAPKs (ERK, JNK, and p38) induced by IL-1β (20 ng/ml) in the primary-cultured chondrocytes of Sprague-Dawley rat.

FIG. 13 illustrates inhibitory effects of the hot-water extract of *Codium fragile* on phophoryltion of MAPKs (ERK, JNK, and p38) induced by IL-1β (20 ng/ml) in the primary-cultured chondrocytes of Sprague-Dawley rat. WECF inhibited ERK, JNK and p38 phosphorylation induced by IL-1β (20 ng/ml). The chondrocytes were pre-treated with WECF (0.5, 1, 2, and 3 mg/ml) for 1 hour, and then, stimulated with IL-1β (20 ng/ml) for 24 hours. ERK, JNK and p38 were confirmed by western blot analysis using a specific antibody. Results of (B, C, D) and A were quantitatively analyzed using Image J-software. Results thereof are exhibited by a mean±SD of three repeated experiments. Symbol * represents statistically significant difference as compared to the LPS-treated group (p<0.01, and *p<0.001).

Figure 14:
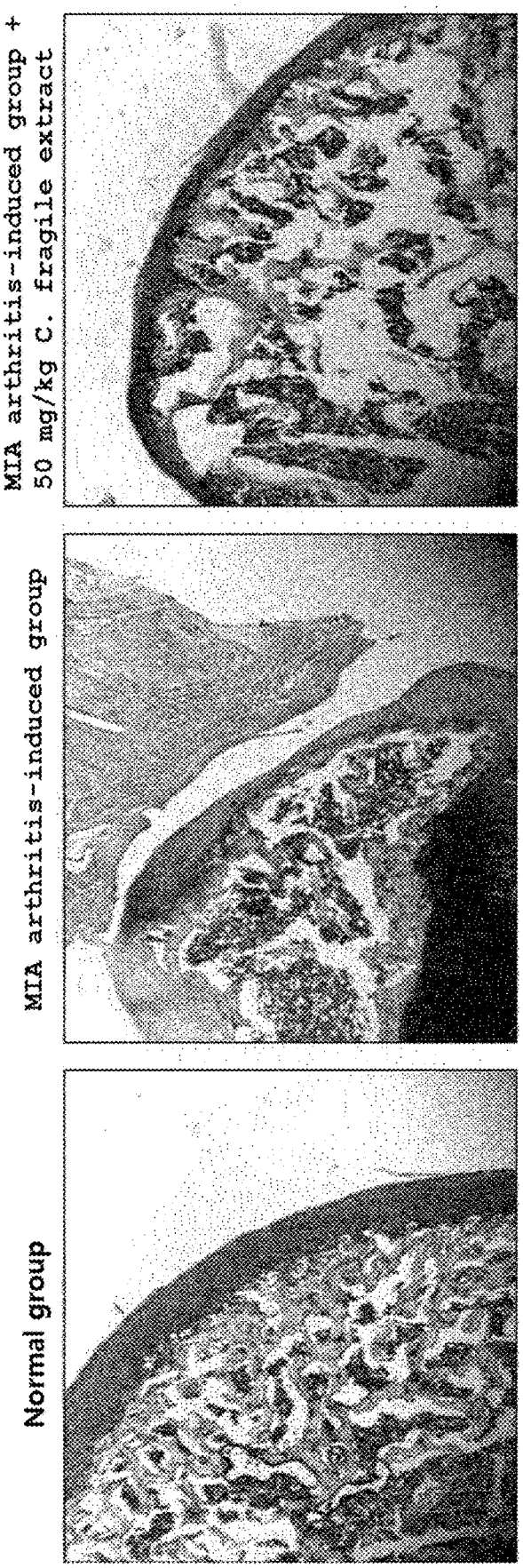
FIG. 14 illustrates effects of increasing synthesis of proteoglycan in monosodium iodoacetate (MIA) osteoarthritis pain model using Sprague-Dawley rat.

FIG. 14 illustrates effects of increasing synthesis of proteoglycan in monosodium iodoacetate (MIA) osteoarthritis pain model using Sprague-Dawley rat. Monosodium iodoacetate (MIA) was dissolved with 10 mg/ml in an injection saline and directly injected through the right knee joint of Sprague-Dawley rat to prepare an osteoarthritis pain model. Then, a control group of 200 μl of sterile water and a test group of the *C. fragile* hot-water extract (50 mg/kg) were orally administered, respectively, to the model using a gastric sonde everyday for 30 days. Thereafter, each joint was excised and demineralized for 4 weeks. After cutting each of the demineralized joint tissues into a piece with a thickness of 10 μm, safranin O staining to stain proteoglycan known as a constituent of the joint, as well as fast-green staining to stain the bone were performed so as to identify joint protective effects of the *C. fragile* hot-water extract.

III. Availability of Composition for Protection or Treatment of Arthritis Based on Experimental Results By integrating the experimental results, the *C. fragile* hot-water extract has been characterized in that: it is biologically safe; inhibits NO activity; inhibits expression of articular cartilage degeneration-inducible materials such as iNOS as an enzyme involved in inflammation and tissue damage, COX-2 related to generation of $PGE_2$ as an inflammation-related factor, IL-1β, IL-6, TNF-α, etc. known as pro-inflammatory cytokines, or the like; and inhibits protein expression of MMP-2, -9, -13 and ADAMTS5 known as articular cartilage matrix degrading enzymes. Further, in the monosodium iodoactate (MIA)-induced arthritis model, expression of proteoglycan protein for constituting the articular cartilage was increased, and effects of treating and preventing osteoarthritis and rheumatoid arthritis were identified. Accordingly, health functional foods including *C. fragile* hot-water extract can be produced. Further, it is considered that taking such foods may be effective in treatment and protection of rheumatoid arthritis as well as osteoarthritis.

As such, the present invention may provide any functional food and quasi-drug type composition with effects of preventing osteoarthritis based on inflammation alleviation and articular cartilage protection, which includes an extract of *Codium fragile* native to South Korea as an effective ingredient. Therefore, although rheumatoid arthritis and osteoarthritis have problems wherein: these are difficult to find an exact cause of the disease and thus do not have effective clinical therapeutics; instead, depend upon physical therapy and pain relief; and entail difficulties in fundamental treatment, the present invention may promote treatment and prevention of such rheumatoid arthritis and osteoarthritis, thereby being helpful in eradicating and preventing modern diseases and health promotion.

The invention claimed is:

1. A method for treating degenerative arthritis, the method comprising administering to a subject in need thereof a pharmaceutical composition, comprising a water extract of *Codium fragile* as an effective ingredient,
   wherein the water extract of *Codium fragile* is prepared by a process comprising:
   drying *Codium fragile*;
   grinding the dried *Codium fragile*; and
   performing an extraction of the ground *Codium fragile* at 95° C. for 1 hour.

* * * * *